(12) United States Patent
Kiepen et al.

(10) Patent No.: US 6,210,339 B1
(45) Date of Patent: Apr. 3, 2001

(54) FLEXIBLE ELONGATE MEMBER HAVING ONE OR MORE ELECTRICAL CONTACTS

(75) Inventors: Horst F. Kiepen, Georgetown; Michael J. Eberle, Fair Oaks; Gary P. Rizzuti, Cameron Park; Daniel A. Brunicardi, Sacramento, all of CA (US)

(73) Assignee: EndoSonics Corporation, Rancho Cordova, CA (US)

( * ) Notice: Subject to any disclaimer, the term of this patent is extended or adjusted under 35 U.S.C. 154(b) by 0 days.

(21) Appl. No.: 09/261,935

(22) Filed: Mar. 3, 1999

(51) Int. Cl.⁷ .............................. A61B 5/02; A61B 5/04; A61B 8/14
(52) U.S. Cl. ................. 600/486; 600/488; 600/459; 600/372; 600/373
(58) Field of Search ...................... 600/481, 485, 600/486, 488, 437, 438, 459, 462, 466, 468, 465, 561, 372, 373, 381; 439/909

(56) References Cited

U.S. PATENT DOCUMENTS

| | | | |
|---|---|---|---|
| Re. 35,648 | * 11/1997 | Tenerz et al. | 600/486 |
| Re. 35,924 | * 10/1998 | Winkler | 600/373 |
| 3,724,274 | * 4/1973 | Millar | 73/726 |
| 4,722,348 | * 2/1988 | Ligtenberg et al. | 600/488 |
| 4,958,642 | 9/1990 | Christian et al. | |
| 4,961,433 | 10/1990 | Christian . | |
| 4,967,753 | 11/1990 | Haase et al. . | |
| 5,059,851 | 10/1991 | Corl et al. . | |
| 5,105,818 | 4/1992 | Christian et al. . | |
| 5,163,445 | 11/1992 | Christian et al. . | |
| 5,174,295 | 12/1992 | Christian et al. . | |
| 5,178,159 | 1/1993 | Christian . | |
| 5,240,437 | 8/1993 | Christian . | |
| 5,348,481 | 9/1994 | Ortiz . | |
| 5,358,409 | 10/1994 | Obara . | |
| 5,413,508 | 5/1995 | Obara . | |
| 5,517,989 | 5/1996 | Frisbie et al. . | |
| 5,701,905 | * 12/1997 | Easch | 600/486 |
| 5,715,827 | 2/1998 | Corl et al. . | |
| 5,795,299 | * 8/1998 | Eaton et al. | 600/459 |
| 5,797,848 | * 8/1998 | Marian et al. | 600/459 |
| 5,797,856 | 8/1998 | Frisbie et al. . | |
| 5,846,205 | * 12/1998 | Curley et al. | 600/472 |
| 5,991,650 | * 11/1999 | Swanson et al. | 600/374 |

* cited by examiner

*Primary Examiner*—Cary O'Connor
*Assistant Examiner*—Navin Natnithitadha
(74) *Attorney, Agent, or Firm*—Leydig, Voit & Mayer, Ltd.

(57) ABSTRACT

A flexible elongate member such as a pressure guide wire (1000) includes an electrical device such as a pressure sensor (1002). The pressure sensor (1002) is electrically connected to conductive bands (304), (306) and (308) located on electrical connector (300). The electrical connector is attached to core wire (602) and shaft or hypotube (704). The use of electrical connector (300) helps minimize the assembly time of pressure guide wire (1000), as well as minimize some of the assembly problems associated with prior art designs such as pressure guide wire (100).

20 Claims, 6 Drawing Sheets

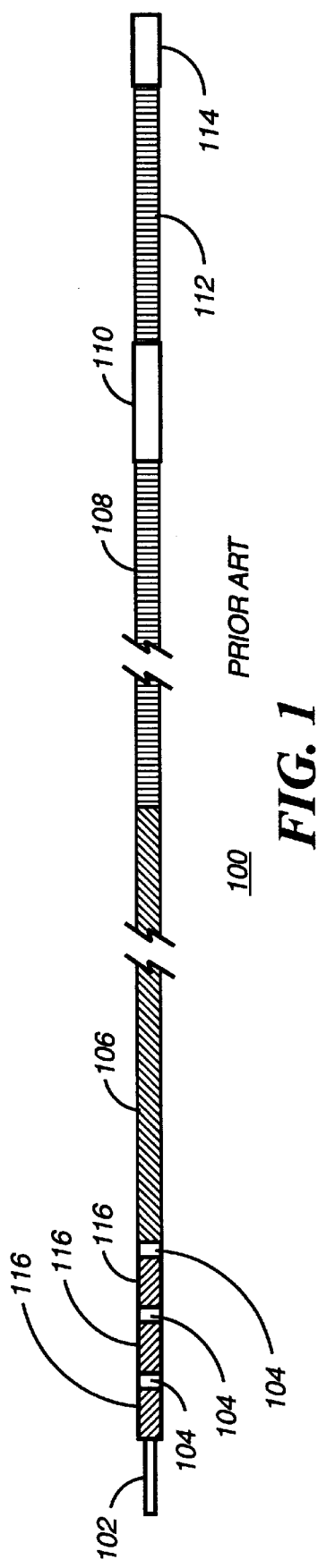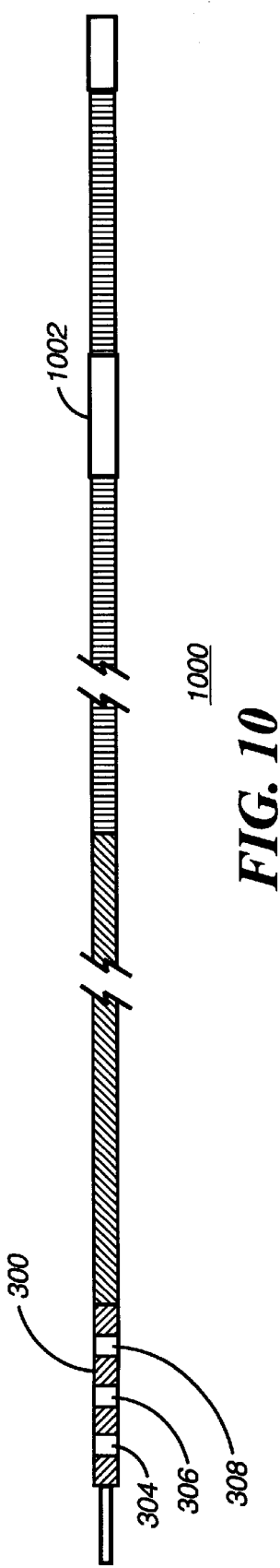

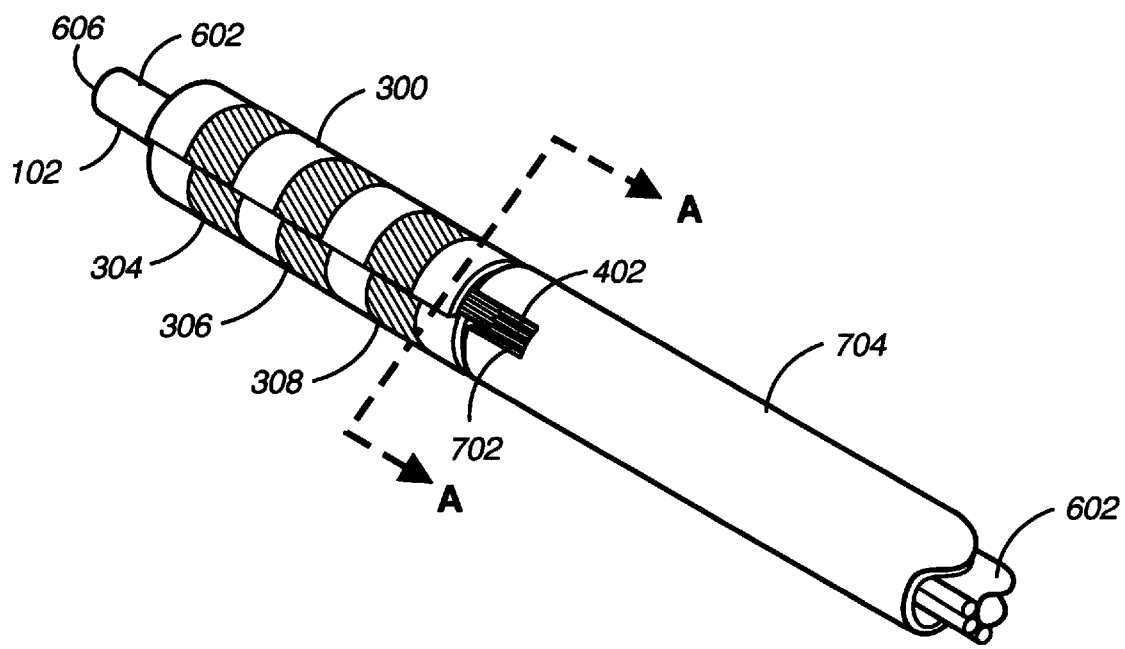
FIG. 7
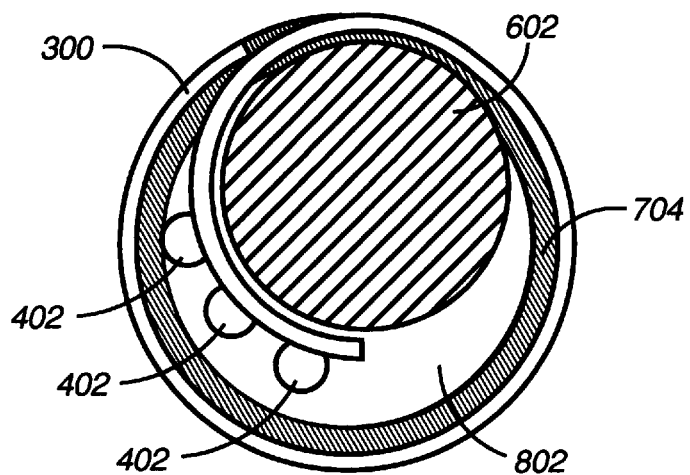
FIG. 8 SECTION A-A

FLEXIBLE ELONGATE MEMBER HAVING ONE OR MORE ELECTRICAL CONTACTS

FIELD OF THE INVENTION

This invention relates in general to the field of medical devices, more particularly, this invention relates to a flexible elongate member such as a medical guide wire or catheter having one or more electrical contacts.

BACKGROUND OF THE INVENTION

Flexible elongate members used in medical applications such as guide wires, catheters, etc., which have electrical devices (e.g., pressure sensors, ultrasound transducers, pressure flow measurement devices, etc.) need to have one or more electrical contacts typically close to the proximal end of the member. The electrical contacts allow for the electrical interconnection of the electrical device found on the flexible elongate member, for example, a pressure sensor, to an external monitoring apparatus.

Currently there is some difficulty in manufacturing small electrical contacts on flexible elongate members such as guide wires having a diameter in the order of 0.018 inch or less. In FIG. 1 there is shown a prior art guide wire 100 having an electrical device in the form of a pressure sensor 110 located in proximity to the distal end of the guide wire 100. Pressure guide wire 100 includes a plurality of electrical contacts 104 separated by insulator bands (spacers) 116 which help form a cylindrical connector located close to the proximal extremity 102 of the pressure guide wire 100. These electrical contacts 104 are electrically interconnected to pressure sensor 110 and allow for the connection of the pressure sensor to an external monitoring apparatus.

The pressure guide wire 100 further includes a shaft also referred to as a hypotube 106 typically formed of stainless steel, a flexible coil member 108 located on one side of the pressure sensor 110, a radiopaque coil 112 located on the other side of pressure sensor 110, and a tip 114. The pressure sensor 110 is electrically interconnected to contacts 104 via a plurality of electrical conductors (not shown), which run through the inside of the flexible is coil 108 and shaft 106.

The cylindrical guide wire connector formed by contacts 104 is interconnected to a female connector 200 shown in FIG. 2. The proximal end 102 of pressure wire 100 is inserted in to the nose section 206 of connector 200 such that contacts 104 become electrical coupled to corresponding contacts located inside of the swivel head 204. The other end of connector 200 includes a pin plug 202, which interconnects to an appropriate monitoring apparatus, in this case a pressure monitor (not shown). In use, the distal end of pressure wire 100 is inserted into a vessel (e.g., artery) of a patient in order to measure the pressure at certain locations along the vessel, which is under investigation.

One problem with pressure guide wire 100 is that the individual electrical contacts 104 are very difficult and expensive to integrate into the guide wire. Contacts 104 are individual metal bands, which are separated by non-electrically conductive spacers 116. During manufacture, each of the individual contacts 104 have to be soldered to the appropriate electrical conductor (not shown, e.g., electrical wire), which is attached to pressure sensor 110.

After the appropriate electrical conductor is soldered or welded to its corresponding contact 104, each individual contact has to be adhesively bonded to the rest of the guide wire 100. The spacers 116 also have to be individually inserted and bonded to the adjacent contact(s) 104. The bonding of the spacers 116 and contacts 104 causes further problems in that the adhesive which bonds them together tends to seep between the joints and has to be removed from the exterior portions of the proximal end of the guide wire 100. Given the small size of the guide wire 100, all of these time consuming steps have to be performed by assembly workers using microscopes which further increase the opportunity for manufacturing mistakes to occur.

Problems can also occur with the contacts 104 or spacers 116 becoming separated from the rest of the assembly due to bad bonding of a particular contact 104 or spacer 116. Another manufacturing problem occurs with the solder joints, which interconnect the electrical conductors coming from pressure sensor 110 to the individual contacts 104. Given that the electrical conductors have to be soldered to the inside surface of the contacts 104, there is very little room in which to solder the contact with a soldering tool, thus some bad solder joints can occur during production.

A need thus exists in the art for a contact assembly, which can overcome the problems associated with the prior art mentioned above.

BRIEF DESCRIPTION OF THE DRAWINGS

FIG. 1 shows a prior art pressure guide wire.

FIG. 7 shows the assembly of FIG. 6 with a shaft attached to the electrical connector in accordance with the invention.

FIG. 8 shows a cross-sectional view of FIG. 7.

FIG. 10 shows a pressure guide wire in accordance with the invention.

DETAILED DESCRIPTION OF THE PREFERRED EMBODIMENT

Figure 3:
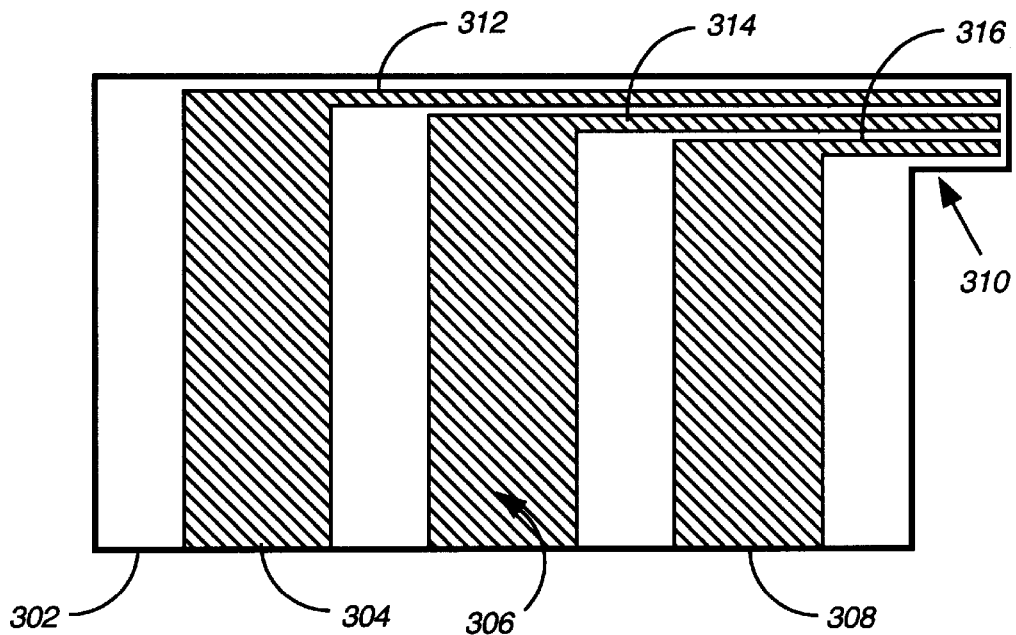
FIG. 3 shows an electrical connector in accordance with the preferred embodiment of the invention before it is rolled-up into a substantially cylindrical shape.

Referring now to the drawings and in particular to FIG. 3, there is shown a circuit carrier (substrate) such as a substantially cylindrical electrical connector 300 comprising substrate 302 and three electrically conductive bands 304, 306 and 308. The electrical connector 300 is the preferred embodiment is formed form a "flex" circuit or flex circuit board 302 which is preferably manufactured from a polyimide such as KAPTON™ manufactured by Dupont, Inc., or other flexible materials used in the art. The thickness of substrate 302 should be such that it can be re-shaped in a relatively tight radius of curvature. The flex circuit could, for example, be of the order of 25 μm thick, or less.

The flexible substrate 302 preferably includes an extension portion 310, which provides termination points for parallel runners 312, 314 and 316 which are interconnected to bands 304, 306 and 308. Runners 312, 314 and 316 have a pitch in the order of 0.002 to 0.004 inch. This pitch is required in order to interface the circuit to the group of electrical wires that travel along the length of the flexible elongate member to the electrical device (e.g., pressure sensor, etc.). Since the guide wire has a small cross-sectional diameter, the wires have to be small, and are therefore close together. Ideally, the pitch of the runners 312, 314 and 316 matches the pitch of the wires so that when the wires are bonded to the flex circuit, there is no need to spread the wires, and the assembly fits within the profile of the flexible elongate member. The wires may be stripped of insulation and attached with conventional means such as soldering or welding.

Figure 4:
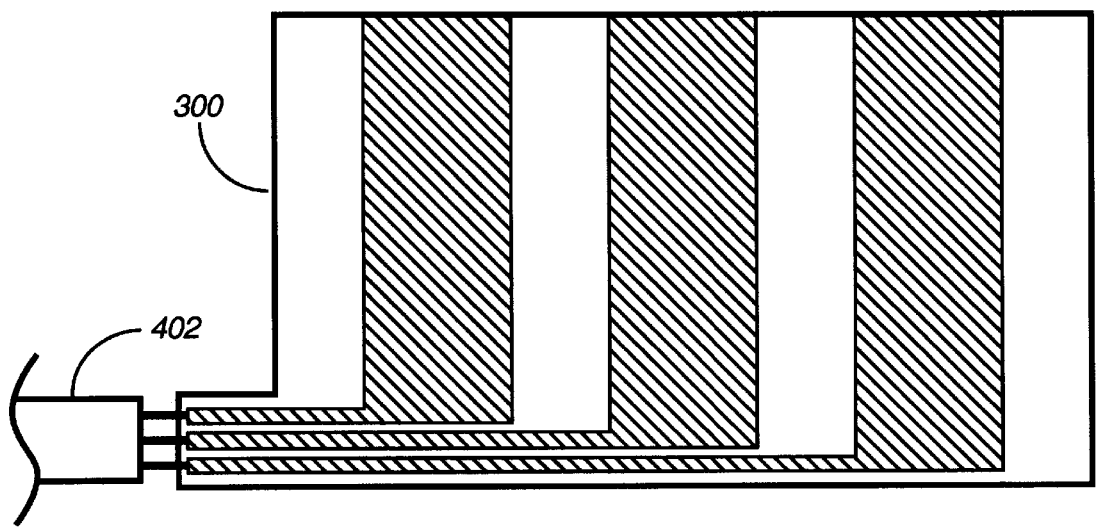
FIG. 4 shows the electrical connector of FIG. 3 interconnected to a plurality of electrical conductors in accordance with the invention.

In FIG. 4 the flexible circuit board 300 is shown attached to three electrical conductors 402 in the form of a cable also known as a trifilar. Each of the bands has a corresponding electrical conductor that is attached by soldering, welding or by another well-known attachment technique.

Figure 5:
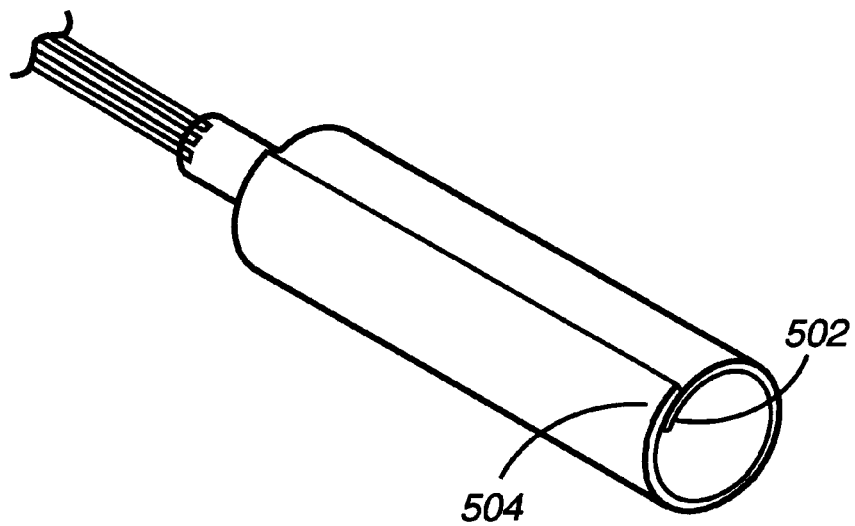
FIG. 5 shows the assembly of FIG. 4 in a rolled-up form.

In FIG. 5 the assembly of FIG. 4 is shown folded in a substantially cylindrical fashion with ends 502, 504 of the flexible circuit board 300 being slightly overlapped in order to pass over the runners 312, 314 and 316. The overlapping maintains the bands 304, 306 and 308 in alignment. The ends of the flexible circuit board are then bonded using any one of a number of conventional adhesives in order for the electrical connector 300 to remain in its substantially cylindrical state. Once bonded, the metallization bands 304, 306 and 308 form three parallel cylindrical bands that run around the periphery of the connector 300. Alternatively, in other designs, the bands 304, 306 and 308 do not have to run around the entire periphery of connector 300.

Figure 6:
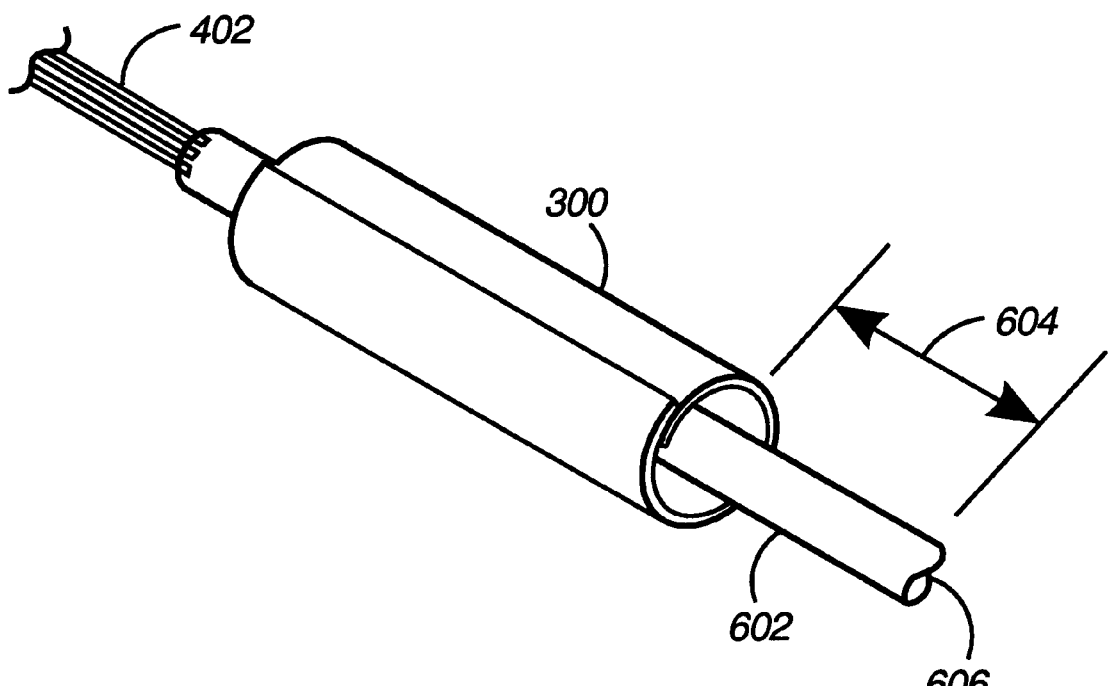
FIG. 6 shows the rolled-up assembly of FIG. 5 mounted to a portion of a core wire.
Figure 11:
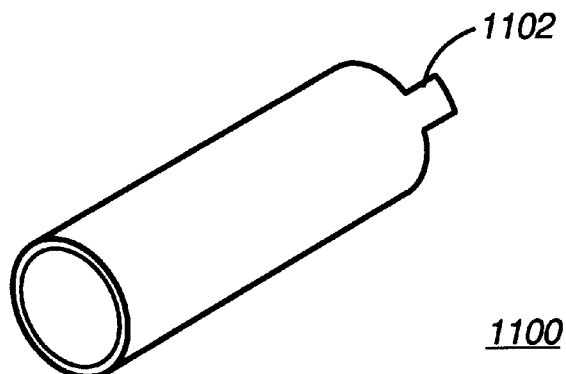
FIG. 11 shows an alternative embodiment in which a tubular substrate is used to form the electrical connector.

In FIG. 6, the electrical connector 300 and cable 402 are shown mounted to a core wire 602 (only a portion shown) which forms the backbone for the pressure guide wire 100. The electrical connector 300 is attached a certain distance 604 from the proximal end 606 of core wire 602. The flexible circuit 300 is filled with adhesive between core wire 602 and the inner surface of the flexible circuit board 300 in order to fix and stiffen the electrical connector 300.

In FIG. 7 the partial guide wire assembly of FIG. 6 is shown with a shaft or hypotube 704 (similar to shaft 106) attached to the electrical connector 300. The electrical connector 300 can be attached to hypotube 704 using one of a number of adhesives such as a polyurethane and oligomer mixture. An optional window 702 is provided in hypotube 704, which could allow for the soldering of insulated electrical conductors 402 after the hypotube and electrical connector 300 have been mated. If optional window 702 is utilized, it is aligned with (also referred to as being in substantial registration with) extension portion 310 found in the substrate 302. Once the electrical conductors 402 are soldered on to the electrical connector 300 the window 702 is covered with insulative "fill" adhesive such as epoxy. A cross-sectional view taken along line A—A is shown in FIG. 8. The electrical connector 300 is attached to core wire 602 using a nonconductive adhesive such as epoxy 802. The epoxy not only serves to attach the flexible circuit board to core wire 602 it also provides a backing material which helps stiffen the flexible circuit board used in this embodiment. The area between the core wire 602 and inner surface of electrical connector 300 is preferably filled with adhesive or other filler in order to stiffen the electrical connector 300.

Figure 2:
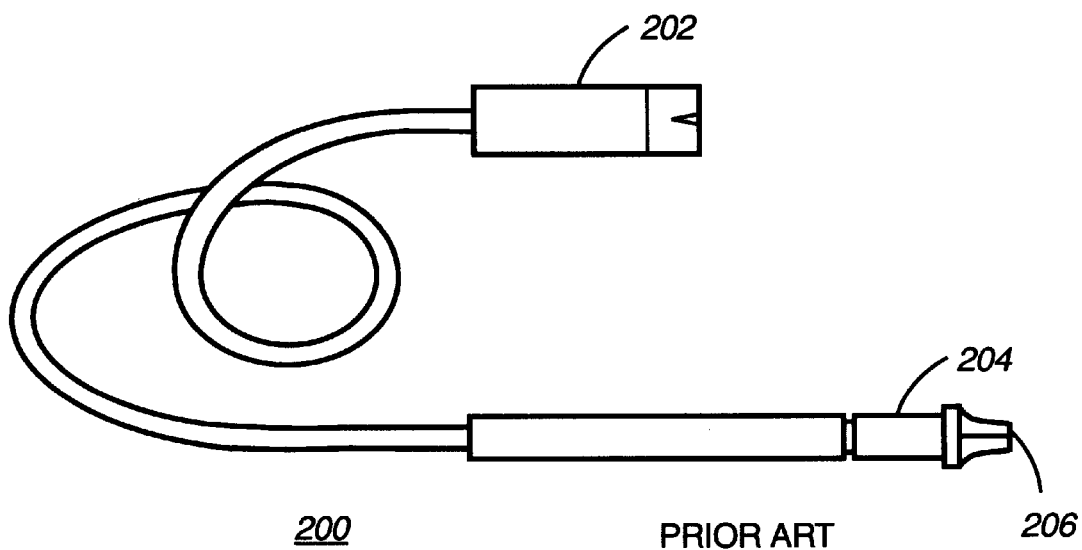
FIG. 2 shows a prior art connector that interconnects the guide wire of FIG. 1 to a monitoring apparatus.
Figure 9:
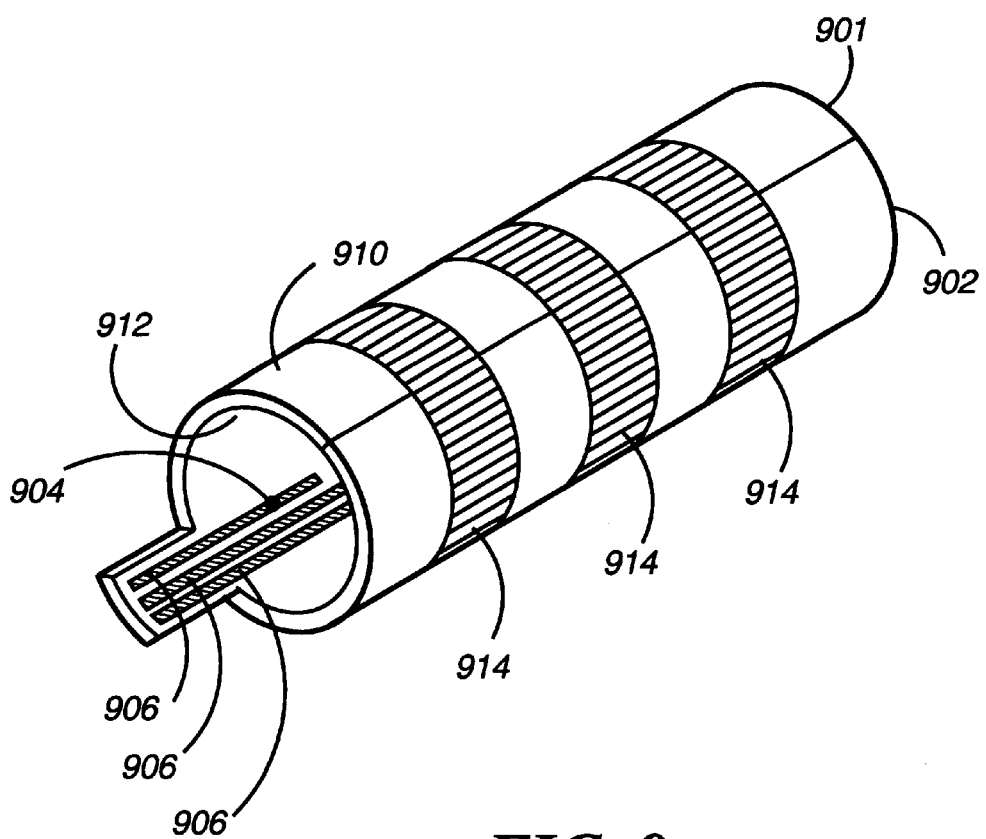
FIG. 9 shows an alternate embodiment of the electrical connector.

An alternate embodiment of the electrical connector of the present invention is shown in FIG. 9. Instead of overlapping the ends of the flexible substrate 302 as shown in FIG. 5 the end portions 901 and 902 of the flexible substrate 302 are bonded substantially flush to each other using adhesive. There is no need to overlap the ends of the flexible substrate in this embodiment as compared to the one-sided embodiment shown in FIG. 5 because in this embodiment the flexible substrate 302 is a two-sided circuit board design. Conductive bands 914 are located on a first surface 910 and corresponding runners 906 are located on a second surface 912. The bands 914 and runners 906 are interconnected using pass-through vias 904.

In FIG. 10 there is shown a pressure guide wire 1000 in accordance with the present invention. Instead of using several individual conductive bands 104 and insulative spacers 116, the pressure guide wire 1000 uses the electrical connector 300 of the present invention. By using the electrical connector 300 of the present invention the time to manufacture the pressure guide wire 1000 is reduced. Also, the problem with the individual bands 104 and spacers 116 becoming detached from the rest of the pressure guide wire assembly as found with the prior art guide wire 100 are eliminated.

Figure 12:
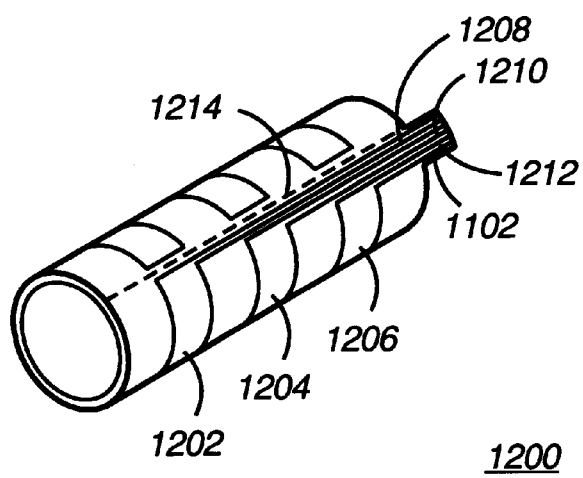
FIG. 12 shows the tubular member of FIG. 11 after metallization of its outer surface.

In an alternate embodiment of the present invention, a tubular member or substrate 1100 is used as the starting point in place of a flexible flat substrate 302 as shown in FIG. 3. Preferably, tubular member 1100 includes an extension portion 1102 similar to extension portion 310. In FIG. 12 cylindrical bands 1202, 1204, 1206 and runners 1208, 1210 and 1212 are added using a conventional metallization technique such as sputtering. Other well-known metallization techniques can be used to attach the metallization to the outside surface of electrical connector 1200.

Figure 13:
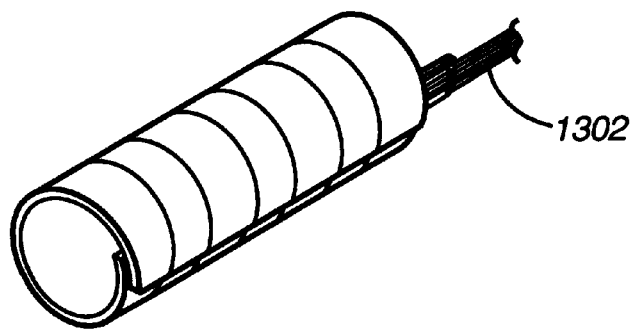
FIG. 13 shows the tubular member of FIG. 12 after it has been cut and overlapped.

A non-metallized area 1214 is left along the length of the tubular member. The non-metallized area is the area in which the tubular member is cut along its entire length. Once cut, the ends of the tubular member are overlapped in order to cross over the three runners 108, 1210 and 1212. Once overlapped as shown in FIG. 13, the outside surface of flexible connector includes three substantially cylindrical metal bands 1202, 1204 and 1206. The overlapped ends are bonded together so the overlapped stated is fixed.

An electrical connector cable 1302 is attached to the runners 1208, 1210 and 1212 at extension 1102. Tubular member 1100 can be formed from a number of materials, which are amenable to metallization such as a polyimide tube. Although the embodiment shown in FIG. 3 requires a flexible circuit substrate since the starting point is a flat substrate, tubular member 1100 can be formed from semi-stiff or stiffer materials if so desired since the member is already in a substantial cylindrical state prior to metallization of its outer surface.

The present invention accomplishes a completely new way of forming an electrical connector on a flexible elongate member such as a cardiovascular guide wire 1000. The invention accomplishes this with a single member that forms the multiple connection requirements. The simplicity of the design also enables rapid and effective assembly techniques, and is compatible with automatic processes that can be performed by machines. The component cost is also reduced compared to the prior art.

The single substrate design can be mass produced using standard photo-lithographic techniques in the case where the flat substrate 302 is used, and standard metallization techniques such as sputtering in the case where the tubular substrate 1100 is utilized as the starting point. The present invention also eliminates a number of previously complicated assembly steps. In addition, the invention allows the electrical device (e.g., pressure sensor, flow sensor, etc.) and electrical conductor 300 to be attached and tested prior to completion of the guide wire 1000.

While the invention has been described in conjunction with specific embodiments, it is evident that many alternatives, modifications, permutations and variations will become apparent to those skilled in the art in light of the foregoing description. For example, although in the present invention the preferred embodiment has been described as a pressure guide wire, other flexible elongate members such as those used to diagnose or treat coronary vascular areas can take advantage of the present invention.

What is claimed is:

1. A pressure guide wire for insertion into humans or animals, comprising:
    a pressure sensor;
    an electrical conductor;
    a circuit carrier forming a substantially cylindrical electrical connector having at least one conductive band on its outer surface;
    an electrical bond connectional electrically connecting the electrical conductor to an electrically conductive path comprising the at least one conductive band; and
    wherein the electrical conductor electrically connects the pressure sensor to the at least one conductive band.

2. A pressure guide wire as defined in claim 1, wherein the circuit carrier is formed from a substantially flat flexible substrate, which is formed into a substantially cylindrical shape.

3. A pressure guide wire as defined in claim 1, wherein the circuit carrier is formed from a tubular member and the tubular member is metallized to form the at least one substantially cylindrical conductive band.

4. A pressure guide wire as defined in claim 1, wherein the circuit carrier further includes an extension portion and wherein the electrical bond connection electrically connecting the electrical conductor to the at least one conductive band is located on the extension portion.

5. A cardiovascular guide wire, comprising:
    a core wire having proximal and distal ends;
    a pressure sensor located in proximity to the distal end of the core wire,
    a substantially cylindrical electrical connector attached about the core wire in proximity to the proximal end of the core wire, the electrical connector having at least one conductive band;
    an electrical bond connection electrically connecting an electrical conductor to an electrically conductive path comprising the at least one conductive band; and
    wherein the electrical conductor electrically connects the pressure sensor to the at least one conductive band.

6. A cardiovascular guide wire as defined in claim 5 further comprising a hypotube coupled to the electrical connector and the electrical conductor runs inside of the hypotube.

7. A cardiovascular guide wire as defined in claim 5, wherein the substantially cylindrical electrical connector is formed from a substantially flat flexible substrate which is folded and overlapped to form the substantially cylindrical connector.

8. A cardiovascular guide wire as defined in claim 5 wherein the substantially cylindrical connector is formed from a substantially flat flexible substrate having first and second end portions and the substantially flat flexible substrate is folded and its first and second end portions are bonded flush together in order to form the substantially cylindrical connector.

9. A cardiovascular guide wire as defined in claim 5, wherein the substantially cylindrical connector is formed from a cylindrical member which has an outer surface which is metallized to form the at least one conductive band.

10. A cardiovascular guide wire as defined in claim 6, wherein the hypotube includes a window and the substantially cylindrical electrical connector includes an extension portion in substantial registration with the window and wherein the electrical bond connection electrically connecting the electrical conductor to the at least one conductive band is located on the extension portion.

11. A flow guide wire for insertion into humans or animals, comprising:
    a flow sensor;
    an electrical conductor;
    a circuit carrier forming a substantially cylindrical electrical connector having at least one conductive band on its outer surface;
    an electrical bond connection electrically connecting the electrical conductor to an electrically conductive path comprising the at least one conductive band; and
    wherein the electrical conductor electrically connects the flow sensor to the at least one conductive band.

12. A flow guide wire as defined in claim 11, wherein the circuit carrier is formed from a substantially flat flexible substrate, which is formed into a substantially cylindrical shape.

13. A flow guide wire as defined in claim 11, wherein the circuit carrier is formed from a tubular member and the tubular member is metallized to form the at least one substantially cylindrical conductive band.

14. A flow guide wire as defined in claim 11, wherein the circuit carrier further includes an extension portion and wherein the electrical bond connection electrically connecting the electrical conductor to the at least one conductive band is located on the extension portion.

15. A cardiovascular guide wire, comprising:
- a core wire having proximal and distal ends;
- a blood flow sensor located in proximity to the distal end of the core wire;
- a substantially cylindrical electrical connector attached about the core wire in proximity to the proximal end of the core wire, the electrical connector having at least one conductive band;
- an electrical bond connection electrically connecting an electrical conductor to an electrically conductive path comprising the at least one conductive band; and
- wherein the electrical conductor electrically connects the blood flow sensor to the at least one conductive band.

16. A cardiovascular guide wire as defined in claim 15, further comprising a hypotube coupled to the electrical connector and the electrical conductor runs inside of the hypotube.

17. A cardiovascular guide wire as defined in claim 15, wherein the substantially cylindrical electrical connector is formed from a substantially flat flexible substrate which is folded and overlapped to form the substantially cylindrical connector.

18. A cardiovascular guide wire as defined in claim 15, wherein the substantially cylindrical connector is formed from a substantially flat flexible substrate having first and second end portions and the substantially flat flexible substrate is folded and its first and second end portions are bonded flush together in order to form the substantially cylindrical connector.

19. A cardiovascular guide wire as defined in claim 15, wherein the substantially cylindrical connector is formed from a cylindrical member which has an outer surface which is metallized to form the at least one conductive band.

20. A cardiovascular guide wire as defined in claim 16, wherein the hypotube includes a window and the substantially cylindrical electrical connector includes an extension portion in substantial registration with the window and wherein the electrical bond connection electrically connecting the electrical conductor to the at least one conductive band is located on the extension portion.

* * * * *